US010131597B2

(12) United States Patent
Wang et al.

(10) Patent No.: US 10,131,597 B2
(45) Date of Patent: *Nov. 20, 2018

(54) PROCESS FOR PRODUCING 2,3,3,3-TETRAFLUOROPROPENE

(71) Applicant: HONEYWELL INTERNATIONAL INC., Morris Plains, NJ (US)

(72) Inventors: Haiyou Wang, Amherst, NY (US); Hsueh Sung Tung, Getzville, NY (US); Selma Bektesevic, Williamsville, NY (US); Daniel C. Merkel, West Seneca, NY (US); Haluk Kopkalli, Staten Island, NY (US); Yuon Chiu, Denville, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,894

(22) PCT Filed: Nov. 2, 2012

(86) PCT No.: PCT/US2012/063331
§ 371 (c)(1),
(2) Date: May 2, 2014

(87) PCT Pub. No.: WO2013/067356
PCT Pub. Date: May 10, 2013

(65) Prior Publication Data
US 2014/0256996 A1 Sep. 11, 2014

Related U.S. Application Data

(60) Provisional application No. 61/555,732, filed on Nov. 4, 2011.

(51) Int. Cl.
C07C 17/20 (2006.01)
B01J 23/26 (2006.01)
C07C 17/087 (2006.01)
C07C 17/25 (2006.01)
C07C 17/42 (2006.01)
B01J 21/04 (2006.01)
B01J 23/34 (2006.01)
B01J 23/745 (2006.01)
B01J 23/75 (2006.01)
B01J 23/755 (2006.01)
B01J 27/10 (2006.01)
B01J 27/12 (2006.01)
B01J 27/138 (2006.01)

(52) U.S. Cl.
CPC ............ C07C 17/202 (2013.01); B01J 21/04 (2013.01); B01J 23/26 (2013.01); B01J 23/34 (2013.01); B01J 23/745 (2013.01); B01J 23/75 (2013.01); B01J 23/755 (2013.01); B01J 27/10 (2013.01); B01J 27/12 (2013.01); B01J 27/138 (2013.01); C07C 17/087 (2013.01); C07C 17/206 (2013.01); C07C 17/25 (2013.01); C07C 17/42 (2013.01)

(58) Field of Classification Search
None
See application file for complete search history.

(56) References Cited

U.S. PATENT DOCUMENTS

| 3,823,195 A * | 7/1974 | Smith ........................... 570/220 |
| 8,058,486 B2 * | 11/2011 | Merkel .................. C01B 7/035 570/135 |
| 8,067,649 B2 * | 11/2011 | Kopkalli ............... C07C 17/087 570/135 |
| 8,754,271 B2 * | 6/2014 | Mukhopadhyay ...... C07C 17/00 570/123 |
| 2009/0240090 A1 | 9/2009 | Merkel et al. |
| 2011/0105807 A1 * | 5/2011 | Kopkalli ............... C01B 7/0718 570/155 |
| 2011/0245548 A1 | 10/2011 | Merkel et al. |

FOREIGN PATENT DOCUMENTS

| CN | 101597209 A | 3/2009 |
| CN | 102026944 A | 4/2011 |
| EP | 2 103 587 A2 | 9/2009 |
| JP | 2009522365 A | 6/2009 |
| JP | 2009-227675 A | 10/2009 |
| JP | 2009227675 A | 10/2009 |
| JP | 2010-534680 A | 11/2010 |
| WO | 2009/015317 A1 | 1/2009 |

(Continued)

OTHER PUBLICATIONS

European Search Report dated May 20, 2015 corresponding to European Patent Appln. No. 1284674308.
Office Action dated Mar. 9, 2015 issued in corresponding U.S. Appl. No. 14/203,823.
Chinese Office Action dated Jul. 23, 2015 to corresponding Chinese Patent Appln. No. 201280065398.6.
Second Office Action issued in Chinese Patent Application No. 201280065398.6 dated Jun. 17, 2016 (in English and Chinese).
SynQuest Laboratories, Inc., Material Safety Data Sheet, pp. 1-4, Oct. 23, 2012.

(Continued)

Primary Examiner — Clinton A Brooks
(74) Attorney, Agent, or Firm — Scully, Scott, Murphy & Presser

(57) ABSTRACT

The present invention relates, in part, to the discovery that, during the fluorination of certain fluoroolefin starting reagents, oligomerization/polymerization of such reagents reduces the conversion process and leads to increased catalyst deactivation. The present invention also illustrates that vaporizing such starting reagents in the presence of one or more organic co-feed reduces such oligomerization/polymerization and improves catalytic stability.

19 Claims, No Drawings

(56) References Cited

FOREIGN PATENT DOCUMENTS

| WO | 2012/051327 A2 | 5/2010 |
| WO | 2010/123148 A1 | 10/2010 |
| WO | 2010/131766 A2 | 11/2010 |
| WO | 2011087825 A1 | 7/2011 |
| WO | 2011/126679 A2 | 10/2011 |

OTHER PUBLICATIONS http://www.guidechem.com/cas-2171211700-31-2.html, CAS No. 21700-31-2 (1,1,1,2,3-Pentachloropropane), 2 pages, accessed Mar. 30, 2016.

Decision on Rejection issued on Patent Application No. 201280065398.6 dated Apr. 12, 2017 in English and Chinese).

Notice of Reasons for Rejection dated Sep. 2, 2016 issued in Application No. 2014-540138 (in English and Japanese).

Notice of Reasons for Rejection dated Jul. 11, 2017 issued in Application No. 2014-540138 with English-language translation thereof.

Notice of Reasons for Rejection (hereinafter "the Notice") dated Mar. 9, 2018 received from the Japanese Patent Office in a corresponding foreign application with English-language translation thereof.

\* cited by examiner

PROCESS FOR PRODUCING 2,3,3,3-TETRAFLUOROPROPENE

CROSS REFERENCE TO RELATED APPLICATIONS

This application is a '371 of PCT Application No. PCT/US2012/063331, filed on Nov. 2, 2012, which claims priority to US Provisional Application Ser. No. 61/555,732 filed on Nov. 4, 2011. the contents of each of the foregoing are incorporated herein by reference.

FIELD OF THE INVENTION

The present invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

However, there remains a need for an economic means of producing hydrofluoroolefins, such as HFO-1234yf. The present invention satisfies this need among others.

SUMMARY OF INVENTION

The present invention relates, in part, to one or more process steps for improving the reaction efficiency used for the production of HFOs, such as 2,3,3,3-tetrafluoropropene (1234yf).

In one aspect, the present invention relates to a process for reducing polymerization of a starting reagent during the manufacture 1234yf by heating a starting reagent composition in a liquid phase that includes at least one compound of formula I, II, and/or III $$CX_2=CCl—CH_2X \quad (I)$$

$$CX_3—CCl=CH_2 \quad (II)$$

$$CX_3—CHCl—CH_2X \quad (III)$$

and an effective amount of one or more co-feed compounds other than the compound of formula I, II, and/or III. "X", as used in any of formulas I, II, and/or III, is independently selected from F, Cl, Br, and I. At least one X is not fluorine. The starting composition is heated so as to form a vapor phase composition.

In a further aspect, the present invention relates to a process for preparing 2-chloro-3,3,3-trifluoropropene by providing, in a liquid phase, a starting composition including at least one compound of formula I, II, and/or III $$CX_2=CCl—CH_2X \quad (I)$$

$$CX_3—CCl=CH_2 \quad (II)$$

$$CX_3—CHCl—CH_2X \quad (III)$$

as defined above, and also an effective amount of one or more organic co-feed compounds, other than the compound of formulas I, II, or III. The starting composition is vaporized to form a vapor phase composition and is then contacted with a fluorinating agent to produce a final composition comprising 2-chloro-3,3,3trifluoropropene.

In either of the foregoing embodiments, or any embodiment provided herein, at least one compound of formula I, II, or III has at least one X is a chlorine. In further embodiments, at least one compound of formula I, II, or III has a chlorine at each X position. In even further embodiments, at least one compound of formula I includes 1,1,2,3-tetrachloropropene and/or at least one compound of formula II includes 2,3,3,3-tetrachloropropene and/or at least one compound of formula III includes 1,1,1,2,3-pentachloropropane.

The organic co-feed compound may be any organic compound that improves the foregoing process, particularly by decreasing starting reagent oligomerization/polymerization and/or reducing catalyst deactivation over the course of the process. In one embodiment, the organic co-feed compound has a boiling point that is lower than the compound of Formula I, II, or III. Such compounds include halocarbons or haloolefins, of which one or more of the following may be included: trichlorofluoropropene (1231), 2,3-dichloro-3,3-difluoropropene (1232xf), 1,2-dichloro-3,3,3-trifluoropropene (1223xd), 2-chloro-3,3,3-trifluoropropene (1233xf), 2 chloro-1,1,1,2-tetrafluoropropane (244bb), 1,1,1,2,2-pentafluoropropane (HFC-245cb), difluoromethane (HFC-32), pentafluoroethane (HFC-125), 1,1,1,2-tetrafluoroethane (HFC-134a), trifluoroethane (HFC-143) (including all isomers thereof), 1,1,1,3,3-pentafluoropropane (HFC-245fa).

The effective amount of the co-feed compound may be any amount provided herein. While not limited thereto, in certain aspects, it is between about 0.1 to about 99.9 wt %, between about 1 to about 50 wt %, between about 3 to about 30 wt %, or between about 5 to about 15 wt %, each based on the total amount of organic feed provided to the reaction.

The step of contacting the starting composition with a fluorinating agent may occur in the presence of a catalyst. In one aspect, the contacting step occurs in a vapor phase with or without the presence of a vapor phase catalyst. Vapor phase catalysts used for such a reaction include, but are not limited to, a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof. In certain embodiments, the catalyst includes a chromium oxide, such as, but not limited to, $Cr_2O_3$.

In even further aspects, the present invention relates to a process for preparing 2,3,3,3-tetrafluoroprop-1-ene by
a. providing a starting composition including a compound of formula I, II, and/or III

$CX_2=CCl-CH_2X$ (I)

$CX_3-CCl=CH_2$ (II)

$CX_3-CHCl-CH_2X$ (III)

wherein X is independently selected from F, Cl, Br, and I, provided that at least one X is not fluorine;
b. vaporizing said starting composition with an effective amount of one or more organic co-feed compounds, other than the compound of formula I, II, or III;
c. contacting the starting composition with a first fluorinating agent to produce a first intermediate composition including 2-chloro-3,3,3-trifluoropropene and a first chlorine-containing byproduct;
d. contacting the first intermediate composition with a second fluorinating agent to produce a second intermediate composition including 2-chloro-1,1,1,2-tetrafluoropropane; and
e. dehydrochlorinating at least a portion of the 2-chloro-1,1,1,2-tetrafluoropropane to produce a reaction product including 2,3,3,3-tetrafluoroprop-1-ene.

Additional embodiments and advantages to the present invention will be readily apparent to one of skill in the art, based on the disclosure provided herein.

DETAILED DESCRIPTION OF THE INVENTION

According to one embodiment, the present invention includes a manufacturing process for making 2,3,3,3-tetrafluoroprop-1-ene using a starting material according to any one or combination of formulas I, II, and/or III:

$CX_2=CCl-CH_2X$ (Formula I)

$CX_3-CCl=CH_2$ (Formula II)

$CX_3-CHCl-CH_2X$ (Formula III)

wherein X is independently selected from F, Cl, Br, and I, provided that at least one X is not fluorine. In certain embodiments, the compound(s) of Formula I, II and/or III contains at least one chlorine, a majority of the Xs as chlorine, or all Xs as chlorine. In certain embodiments, the compound(s) of formula I includes 1,1,2,3-tetrachloropropene (1230xa). In certain embodiments, the compound(s) of formula II includes 2,3,3,3-tetrachloropropene (1230xf). In further embodiments, the compound(s) of formula III includes 1,1,1,2,3-pentachloropropane (240db). Processes applicable to the present invention include, without limitation, integrated multistep processes as described in U.S. Pat. No. 8,084,653 and US Published Patent Application 2009/0240090, the contents of each of which are incorporated herein by reference.

The method generally includes at least three reaction steps. In the first step, a starting composition of Formulas I, II, and/or III (such as 1,1,2,3-tetrachloropropene, 2,3,3,3-tetrachloropropene, and/or 1,1,1,2,3-pentachloropropane) is reacted with anhydrous HF in a first vapor phase reactor (fluorination reactor) to produce a mixture of 2-chloro-3,3,3-trifluoropropene (1233xf) and HCl. In certain embodiments, the starting reagents are provided as a liquid phase and, prior to the reaction, are heated in a vaporizer to form a vapor phase. To this end, the conversion of the compounds of formulas I, II, and/or III occurs in the vapor phase and in the presence of a vapor phase catalyst. One non-limiting catalyst may include, but is not limited to, a fluorinated chromium oxide. The catalyst may (or may not) have to be activated with anhydrous hydrogen fluoride HF (hydrogen fluoride gas) before use depending on the state of the catalyst. In one embodiment, there is no oxygen-containing agent or gas feed, e.g. air, pure oxygen, or diluted oxygen gas, such as an oxygen/inert gas (e.g. nitrogen), to the first vapor phase reactor.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/$carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

The compound of formulas I, II, and/or III is also provided to the vaporizer with at least one co-feed organic compound and, optionally but preferably, hydrogen fluoride. The compound preferably, though not exclusively, has a boiling point that is lower than the compound of Formula I, II, or III and should be chemically compatible with both the compound of these formulas and hydrogen fluoride. Generally speaking, such compounds may include any halocarbon or haloolefin that exhibits the desired improvement in the reaction and/or improvement in the catalyst life. Non-limiting examples of such halocarbons and haloolefins include one or any combination of trichlorofluoropropene (1231), 2,3-dichloro-3,3-difluoropropene (1232xf), 1,2-dichloro-3,3,3-trifluoropropene (1223xd), 2-chloro-3,3,3-trifluoropropene (1233xf), 2 chloro-1,1,1,2-tetrafluoropropane (244bb), 1,1,1,2,2-pentafluoropropane (HFC-245cb), difluoromethane (HFC-32), pentafluoroethane (HFC-125), 1,1,1,2-tetrafluoroethane (HFC-134a), trifluoroethane (HFC-143) (including all isomers thereof), 1,1,1,3,3-pentafluoropropane (HFC-245fa). In certain embodiments, the halocarbons and haloolefins include one or more organic compounds that are typically generated during the fluorination reaction of 1230xa with HF, such as, but not limited to, 1231, 1232xf, 1223xd, 1233xf, 244bb, HFC-245cb, and combinations thereof.

The amount of co-feed compounds or an "effective amount," as used herein, relates to any amount of co-feed provided to the vaporizer that may be used to improve the conversion of a compound of formula I, II, and/or III (particularly 1230xa, 1230xf, and/or 240db) to 1233xf in the downstream reaction. In one aspect, the effective amount of co-feed organic compound may be any amount that measurably reduces the occurrence of oligomerization/polymerization of the compound of the forgoing formulas during steam vaporization or during the fluorination reaction. Similarly, an effective amount may also, or independently, include any amount of the organic co-feed that results in a measurable reduction of catalyst deactivation, particularly deactivation caused by starting reagent oligomerization/polymerization. In one non-limiting embodiment, the percentage of co-feed organic(s) in total organic feed can be ranged from 0.1 to 99.9 wt %, from 1 to 50 wt %, from 3 to 30 wt %, or from 5 to 15 wt %, each based upon the total weight of organic reagents used. While not intending to be bound by theory, it is believed that co-feeding at least an organic compound with a boiling point lower than the compound of formula I, II, or III (particularly 1230xa, 1230xf, or 240db) can facilitate the vaporization of the starting compounds since the bubble point of the mixture is lower than that of the starting compounds and can help avoid or at least reduce the formation of starting reagent oligomers and/or polymer.

A vaporizer, as described herein, relates to a heat exchanger designed to convert a chemical compound from liquid form into vapor form. Often the heating medium is steam, and hence steam vaporizer is preferred. The vaporizer is preferably, though not exclusively, made from corrosion-resistant materials. Non-limiting examples of corrosion-resistant materials include Hastelloy, Nickel, Incoloy, Inconel, Monel and fluoropolymer linings.

In a certain embodiments, liquid 1230xa, HF, and one or more of the co-feeds are fed continuously to a steam vaporizer. The steam pressure can be varied in a wide range from 30 to 250 psig, preferably from 100-200 psig, and even more preferably from 140-160 psig. The mol ratio of HF to HCO-1230xa is 1:1 to 50:1 and preferably from about 10:1 to about 20:1. Depending on the pressure of down-stream reactor, the vaporizer can be operated at a pressure of 200 psig or lower, preferably 100 psig or lower, and even more preferably 70 psig or lower. The process temperature at the outlet of the vaporizer is inherently determined by its dimension and efficiency as well as steam and process conditions.

In further embodiments, liquid 1230xf, HF, and one or more of the co-feeds are fed continuously to a steam vaporizer. The steam pressure can be varied in a wide range from 30 to 250 psig, preferably from 100-200 psig, and even more preferably from 140-160 psig. The mol ratio of HF to HCO-1230xf is 1:1 to 50:1 and preferably from about 10:1 to about 20:1. Depending on the pressure of down-stream reactor, the vaporizer can be operated at a pressure of 200 psig or lower, preferably 100 psig or lower, and even more preferably 70 psig or lower. The process temperature at the outlet of the vaporizer is inherently determined by its dimension and efficiency as well as steam and process conditions.

In even further embodiments, liquid 240db, HF, and one or more of the co-feeds are fed continuously to a steam vaporizer. The steam pressure can be varied in a wide range from 30 to 250 psig, preferably from 100-200 psig, and even more preferably from 140-160 psig. The mol ratio of HF to 240db is 1:1 to 50:1 and preferably from about 10:1 to about 20:1. Depending on the pressure of down-stream reactor, the vaporizer can be operated at a pressure of 200 psig or lower, preferably 100 psig or lower, and even more preferably 70 psig or lower. The process temperature at the outlet of the vaporizer is inherently determined by its dimension and efficiency as well as steam and process conditions.

In any of the foregoing embodiments, the vaporized mixture is then fed into a fluorination reactor charged with a fluorinated chromia catalyst to convert the starting material(s) into 1233xf. The fluorination reaction may be carried out at a temperature from about 150° C. to about 400° C. (preferably from about 180° C. to about 300° C.) and at a pressure from about 0 psig to about 200 psig, preferably from about 0 psig to about 100 psig, and even more preferably from 0 psig to 70 psig. Contact time of organic feeds with the catalyst may range from about 1 second to about 60 seconds, however, longer or shorter times can be used.

The fluorination reaction is preferably carried out to attain a conversion of about 50% or, preferably, about 90% or higher. Conversion is calculated by the number of moles of reactant consumed divided by number of moles of reactant fed to the reactor multiplied by 100. The selectivity for 1233xf attained is preferably about 60% or higher and more preferably about 80% or higher. Selectivity is calculated by number of moles of product (1233xf) formed divided by number of moles of reactant consumed.

This first step of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings. The vessel is a fixed catalyst bed or fluidized bed. If desired, inert gases such as nitrogen or argon may be employed in the reactor during operation.

In general, the effluent from the fluorination reaction step, including any intermediate effluents that may be present in multi-stage reactor arrangements, may be processed to achieve desired degrees of separation and/or other processing. For example, in embodiments in which the reactor effluent includes 1233xf, the effluent will generally also include HCl and one or more of HF, 2,3-dichloro-3,3-difluoropropene (1232xf), 1,2-dichloro-3,3,3-trifluoropropene (1223xd), trichlorofluoropropene (1231) isomers, 2 chloro-1,1,1,2-tetrafluoropropane (244bb), and unreacted 1230xa, 1230xf, and/or 240db. Some portion or substantially all of these components of the reaction product may be recovered from the reaction mixture via any separation or purification method known in the art such as neutralization and distillation. It is expected that unreacted starting materials and HF could be recycled, completely or partially, to improve the overall yield of the desired 1233xf. 1232xf and any 1231 formed may also be recycled.

Optionally, hydrogen chloride is then recovered from the result of the fluorination reaction. Recovering of hydrogen chloride is conducted by conventional distillation where it is removed from the distillate. Alternatively, HCl can be recovered or removed by using water or caustic scrubbers. When a water extractor is used, HCl is removed as an aqueous solution. When caustic scrubbers are used, HCl is just removed from system as a chloride salt in aqueous solution.

In the second step of the process for forming 2,3,3,3-tetrafluoroprop-1-ene, 1233xf is converted to 2-chloro-1,1,1,2-tetrafluoropropane (244bb). In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the 1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and F. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Preferred, but non-limiting, catalysts include activated carbon, stainless steel (e.g. SS 316), austenitic nickel-based alloys (e.g. Inconel 625), nickel, fluorinated 10% CsCl/MgO, and 10% $CsCl/MgF_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

In one embodiment, the organic co-feed compounds are provided as fresh feeds in effective amounts, i.e. they are not obtained from recycle streams derived from the multistep process.

In another embodiment, the organic co-feeds compounds are present in one or more recycle streams derived from the multistep process as described in U.S. Pat. No. 8,084,653 and US Published Patent Application 2009/0240090. In a practice of this embodiment, the invention is directed to a multistep process for preparing 2,3,3,3-tetrafluoropropene (1234yf) comprising a.) providing, in a liquid phase, 1,1,2,3-tetrachloropropene (1230xa), a fluorinating agent, and at least one organic co-feed compound, to a vaporizer; b.) vaporizing said 1,1,2,3-tetrachloropropene (1230xa), said fluorinating agent, and said at least one organic co-feed compound, to form a vaporized mixture; c.) contacting, in a first vapor phase reactor, said vaporized mixture with at least one compound of formula (I)

$$CX_2=CCl-CH_2X \quad (I)$$

wherein X is independently selected from F, Cl, Br, and I, provided that at least one X is not fluorine, optionally in the presence of a vapor phase catalyst, to produce a first intermediate composition comprising 2-chloro-3,3,3trifluoropropene (1233xf) and HCl; b.) separating said HCl and said 2-chloro-3,3,3trifluoropropene (1233xf) from said first intermediate composition;

c.) contacting, in a liquid phase reactor, said separated 2-chloro-3,3,3trifluoropropene (1233xf) with a second fluorinating agent to produce a second intermediate composition comprising 2-chloro-1,1,1,2-tetrafluoropropane (244bb); and e). dehydrochlorinating, in a second vapor phase reactor, at least a portion of said 2-chloro-1,1,1,2-tetrafluoropropane (244bb) to produce a reaction product comprising 2,3,3,3-tetrafluoropropene. In another practice of this embodiment, said first intermediate composition further comprises at least one organic co-feed compound. In another practice, the process further comprised, in step b.), separating said at least one organic co-feed compound from said first intermediate composition, and recycling an effective amount of said separated at least one organic co-feed compound to said vaporizer in step a.). In one embodiment of this practice, said recycle is substantially free of 244bb and/or 245cb, or contains these materials in amounts that are not effective amounts. In another practice, the organic co-feed compounds are provided to the vaporizer as a combination of fresh feeds and recycle. In another practice, the process comprises, step a.), said at least one organic co-feed be present in an effective amount and thereby reducing the formation of oligomers and/or polymers in said vaporizer. In another practice, said fluorinating agent is HF, and said optional vapor phase catalyst is a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof.

The following are examples of the invention and are not to be construed as limiting.

EXAMPLES

Example 1

This example illustrates the effect of co-feeding 1232xf or 1233xf together with 1230xa and HF on the vaporization of 1230xa and the formation of non-volatile residue.

A system consisting of $N_2$, HF, and organic feed systems, steam vaporizer, 3/4" OD U-shaped super-heater (immersed in sandbath), and acid scrubber was used for the vaporization study. High pressure (150 psig) steam at full rate was used to heat up the vaporizer. The process pressure was controlled by controlling the pressure in U-shaped super-heater, which was kept at 180° C. HF and organic (1230xa, 10% 1232xf/90% 1230xa, or 10% 1233xf/90% 1230xa) were introduced to the steam vaporizer and then the U-shaped super-heater at feed rates of 2.0 lb/h and 1.0 lb/h, respectively. After eight hours, the mixed feed and the steam were stopped, and the vaporizer was cooled down in nitrogen flow. At room temperature, the content accumulated in the steam vaporizer was drained and weighed. After that water and methylene chloride were added into the drained sample and phase separation was performed. A fraction of the separated organic phase was subject to non-volatile residual (NVR) determination. As shown in Table 1, the co-feeding of 1232xf or 1233xf significantly reduced the build-up in steam vaporizer except for 20 psig pressure point and the total amount of NVR in all pressures.

TABLE 1

| System | % of drained org. in total fed org. | | | Total residue | | |
| --- | --- | --- | --- | --- | --- | --- |
|  | 20 psig | 70 psig | 100 psig | 20 psig | 70 psig | 100 psig |
| 1230xa/HF | 2.8 | 11.6 | 10.5 | 6964 | 5223 | 8771 |
| 10% 1232xf-90% 1230xa/HF | 3.7 | 3.4 | 3.4 | 3502 | 1790 | 1546 |
| 10% 1233xf-90% 1230xa/HF | 3.6 | 2.6 | 3.0 | 1524 | 1106 | 1386 |

Example 2

The 1230xa used in this example contained 5 ppm di-isopropyl amine. A mixture of 10 wt % 1233xf-90 wt %1230xa was made as feedstock. 6.5 L of pre-fluorinated chromium oxide catalyst was loaded into a 4 inch Monel 400 reactor. The reactor was heated up to about 180° C. in nitrogen flow. Anhydrous HF feed was then started at a flow rate of 1.9 lb/h. After passing though a Mol Sieve 3A column at a flow rate of 1.1 lb/h, organic feed was combined with HF feed. The mixed HF and organic feed was introduced to a vaporizer for vaporization and then to the reactor for reaction. The reaction temperature (hot spot temperature) was increased to about 200° C. once the reaction was initiated. The reactor pressure was set at 70 psig. Samples were periodically taken from the product stream and were analyzed by GC and GC-MS during reaction. The results showed that 1230xa conversion was almost 100% and the average selectivities to 1233xf, 1232xf, 244bb were about 97.9%, 0.3%, and 1.5%, respectively, during the period of time of the reaction study that lasted for about 300 hours.

What is claimed is:

1. A process for reducing polymerization of a starting composition comprising:
   providing a liquid phase composition comprising an organic compound of formulas I, II, and/or III $CX_2=CClCH_2X$ (Formula I)

$CX_3—CCl=CH_2$ (Formula II)

$CX_3—CHCl—CH_2X$ (Formula III)

and one or more organic co-feed compounds, other than the compound of formulas I, II, and/or III, the one or more organic co-feed compounds being present in an effective amount to reduce polymerization of the compound of Formula I, II and/or III, said effective amount ranging from about 3 to about 50 wt % based on the total weight of the organic compound Formulas I, II, and/or III and the one or more organic co-feed compounds, and optionally hydrogen fluoride, wherein X is independently selected from F, Cl, Br, and I, provided that at least one X is not fluorine; and
   heating said starting composition to form a vapor phase composition.

2. The process of claim 1, wherein the organic co-feed compound is a halocarbon or haloolefin.

3. The process of claim 1, wherein the organic co-feed compound is selected from the group consisting of trichlorofluoropropene (1231), 2,3-dichloro-3,3-difluoropropene (1232xf), 1,2-dichloro-3,3,3-trifluoropropene (1223xd), 2-chloro-3,3,3-trifluoropropene (1233xf), 2-chloro-1,1,1,2-tetrafluoropropane (244bb), 1,1,1,2,2-pentafluoropropane (HFC-245cb), difluoromethane (HFC-32), pentafluoroethane (HFC-125), 1,1,1,2-tetrafluoroethane (HFC-134a), trifluoroethane (HFC-143), 1,1,1,3,3-pentafluoropropane (HFC-245fa) and combinations thereof.

4. The process of claim 1, wherein the effective amount of organic co-feed compound is between about 5 to about 15 wt %.

5. The process of claim 1 wherein the effective amount of organic co-feed is between about 3 to about 30 wt %.

6. The process of claim 1 wherein the organic co-feed compound has a boiling point lower than the boiling point of the organic compound of formulas I, II, or III.

7. A process for preparing 2-chloro-3,3,3-trifluoropropene comprising:
   providing, in a liquid phase, a starting composition comprising at least one organic compound of formulas I, II, and/or III:

$CX_2=CCl-CH_2X$ (Formula I)

$CX_3-CCl=CH_2$ (Formula II)

$CX_3-CHCl-CH_2X$ (Formula III)

wherein X is independently selected from F, Cl, Br, and I, provided that at least one X is not fluorine;

vaporizing said starting composition with an effective amount of one or more organic co-feed compounds, other than the compound of formula I, II, and/or III to form a vapor phase composition, wherein said one or more organic co-feed compounds are present in an effective amount to reduce polymerization of the compound of Formula I, II and/or III, said effective amount ranging from about 3 to about 50 wt % based on the total weight of the organic compound of Formulas I, II and/or III and the organic co-feed; and contacting said vaporized starting composition with a fluorinating agent to produce a final composition comprising 2-chloro-3,3,3trifluoropropene.

8. The process of claim 7, wherein the organic co-feed compound is a halocarbon or haloolefin.

9. The process of claim 7, wherein the organic co-feed compound is selected from the group consisting of trichlorofluoropropene (1231), 2,3-dichloro-3,3-difluoropropene (1232xf), 1,2-dichloro-3,3,3-trifluoropropene (1223xd), 2-chloro-3,3,3-trifluoropropene (1233xf), 2-chloro-1,1,1,2-tetrafluoropropane (244bb), 1,1,1,2,2-pentafluoropropane (HFC-245cb), difluoromethane (HFC-32), pentafluoroethane (HFC-125), 1,1,1,2-tetrafluoroethane (HFC-134a), trifluoroethane (HFC-143), 1,1,1,3,3-pentafluoropropane (HFC-245fa) and combinations thereof.

10. The process of claim 7, wherein the effective amount of organic co-feed compound is between about 5 to about 15 wt %.

11. The process of claim 7, wherein at least one compound of formula I, II, or III is a compound comprising at least one X is chlorine.

12. The process of claim 7, wherein at least one compound of formula I, II, or III is a compound where all Xs are chlorine.

13. The process of claim 7, wherein the at least one compound is 1,1,2,3-tetrachloropropene, 2,3,3,3-tetrachloropropene or 1,1,1,2,3-pentachloropropane.

14. The process of claim 7, wherein the contacting of said starting composition with a fluorinating agent occurs in a vapor phase.

15. The process of claim 14, wherein the contacting step occurs in the presence of a vapor phase catalyst.

16. The process of claim 15, wherein the vapor phase catalyst is selected from the group consisting of a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof.

17. The process of claim 16 wherein the catalyst comprises a chromium oxide.

18. The process of claim 7 wherein the effective amount of organic co-feed is between about 3 to about 30 wt %.

19. The process of claim 7 wherein the organic co-feed compound has a boiling point lower than the boiling point of the organic compound of formulas I, II, or III.

* * * * *